United States Patent
Schmidt

(10) Patent No.: US 11,139,508 B2
(45) Date of Patent: Oct. 5, 2021

(54) LITHIUM SALT MIXTURE AND USES THEREOF AS A BATTERY ELECTROLYTE

(71) Applicant: Arkema France, Colombes (FR)

(72) Inventor: Grégory Schmidt, St Andéol le Château (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/500,011

(22) PCT Filed: Apr. 3, 2018

(86) PCT No.: PCT/FR2018/050825
§ 371 (c)(1),
(2) Date: Oct. 1, 2019

(87) PCT Pub. No.: WO2018/185422
PCT Pub. Date: Oct. 11, 2018

(65) Prior Publication Data
US 2020/0119397 A1    Apr. 16, 2020

(30) Foreign Application Priority Data

Apr. 4, 2017 (FR) ...................................... 1752915

(51) Int. Cl.
| | | |
|---|---|---|
| *H01M 10/0567* | (2010.01) | |
| *H01M 10/0569* | (2010.01) | |
| *H01M 4/02* | (2006.01) | |

(52) U.S. Cl.
CPC ... *H01M 10/0567* (2013.01); *H01M 10/0569* (2013.01); *H01M 2004/027* (2013.01); *H01M 2004/028* (2013.01)

(58) Field of Classification Search
CPC ......... H01M 10/0525; H01M 10/0567; H01M 10/0568; H01M 10/0569; H01M 2300/0025; H01M 2300/0037; C07D 233/90; Y02E 60/10
See application file for complete search history.

(56) References Cited

U.S. PATENT DOCUMENTS

| | | | |
|---|---|---|---|
| 2014/0315079 A1 | 10/2014 | Schmidt et al. | |
| 2015/0017551 A1* | 1/2015 | Schmidt | C07D 233/90 |
| | | | 429/326 |
| 2016/0126589 A1 | 5/2016 | Xiao et al. | |
| 2017/0047607 A1 | 2/2017 | Schmidt et al. | |
| 2018/0034106 A1 | 2/2018 | Schmidt | |
| 2018/0076485 A1* | 3/2018 | Zhang | H01M 4/625 |

FOREIGN PATENT DOCUMENTS

| | | |
|---|---|---|
| FR | 2983466 A1 | 6/2013 |
| WO | 2013072591 A1 | 5/2013 |
| WO | 2015158979 A1 | 10/2015 |
| WO | 2016146925 A1 | 9/2016 |

OTHER PUBLICATIONS

International Search Report (PCT/ISA/210) dated Jun. 20, 2018, by the European Patent Office as the International Searching Authority for International Application No. PCT/FR2018/050825.
Written Opinion (PCT/ISA/237) dated Jun. 20, 2018, by the European Patent Office as the International Searching Authority for International Application No. PCT/FR2018/050825.

* cited by examiner

*Primary Examiner* — Brittany L Raymond
(74) *Attorney, Agent, or Firm* — Buchanan Ingersoll & Rooney P.C.

(57) ABSTRACT

A lithium salt mixture comprising: from 85% to 99.9 mol % of lithium bis(fluorosulfonyl)imidide; and from 0.1% to 15 mol % of lithium 2-trifluoromethyl-4,5-dicyano-imidazolate. Also, an electrolyte composition containing same and to the uses thereof. Also, an electrochemical cell including a negative electrode, a positive electrode and the electrolyte composition interposed between the negative electrode and the positive electrode. Also, a battery containing at least one electrochemical cell with the electrolyte composition.

14 Claims, No Drawings

LITHIUM SALT MIXTURE AND USES THEREOF AS A BATTERY ELECTROLYTE

FIELD OF THE INVENTION

The present patent application relates to a mixture of lithium salts, and to its use as battery electrolyte.

TECHNICAL BACKGROUND

A lithium-ion battery or a Li-sulfur battery comprises at least a negative electrode (anode), a positive electrode (cathode), a separator and an electrolyte. The electrolyte is generally composed of a lithium salt dissolved in a solvent which is generally a mixture of organic carbonates, in order to have a good compromise between the viscosity and the dielectric constant. Additives can subsequently be added in order to improve the stability of the electrolyte salts.

The most widely used salts include $LiPF_6$ (lithium hexafluorophosphate), which has several of the qualities required but exhibits the disadvantage of decomposing to form hydrofluoric acid (HF) by reaction with water. The HF formed can result in a dissolution of the cathode material. The reaction of $LiPF_6$ with the residual water thus affects the longevity of the battery and can cause safety problems, in particular in the context of the use of lithium-ion batteries in specific vehicles.

Other salts have thus been developed, such as LiTFSI (lithium bis(trifluoromethanesulfonyl)imide) and LiFSI (lithium bis(fluorosulfonyl)imide). These salts exhibit only little or no spontaneous decomposition and are more stable with regard to hydrolysis than $LiPF_6$. Nevertheless, LiTFSI exhibits the disadvantage of being corrosive for current collectors, in particular those made of aluminum.

In the field of batteries, there exists an ongoing need for the development of novel salts which make it possible to improve the performance qualities of the battery, such as the lifetime, and/or the cycling stability, and/or the decrease in the irreversible capacity of the battery, the power performance qualities, in particular over a wide temperature range, such as, for example, from −25° C. approximately to 60° C. approximately.

DESCRIPTION OF THE INVENTION

Mixture

The present patent application relates to a mixture of lithium salts comprising:
- from 85 mol % to 99.9 mol % of lithium bis(fluorosulfonyl)imide (LiFSI); and
- from 0.1 mol % to 15 mol % of lithium 2-trifluoromethyl-4,5-dicyanoimidazolate (LiTDI).

According to the invention, the molar percentages are with respect to the total number of moles of the compounds of the mixture.

In the context of the invention, the terms "lithium bis(fluorosulfonyl)imide salt", "lithium bis(sulfonyl)imide", "LiFSI", "$LiN(FSO_2)_2$", "lithium bis(sulfonyl)imide" and "lithium bis(fluorosulfonyl)imide" are used equivalently.

In the context of the invention, the "total number of moles of the compounds of the mixture" corresponds to the sum of the number of moles of each compound of the mixture.

Lithium 2-trifluoromethyl-4,5-dicyanoimidazolate, known under the name LiTDI, has the following structure:

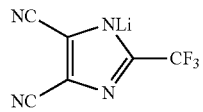

According to one embodiment, the abovementioned mixture is composed essentially of, preferably consists of:
- from 85 mol % to 99.9 mol % of lithium bis(fluorosulfonyl)imide (LiFSI); and
- from 0.1 mol % to 15 mol % of lithium 2-trifluoromethyl-4,5-dicyanoimidazolate (LiTDI).

Impurities can be present in the mixtures, in a proportion, for example, of less than 3000 ppm, preferably of less than 1000 ppm, in particular of less than 500 ppm, with respect to the total weight of said mixture.

In the context of the invention, the term "ppm" or "parts per million" is understood to mean ppm by weight.

According to one embodiment, the mixture according to the invention comprises (preferably is composed essentially of, and preferentially consists of):

LiFSI in one of the following molar percentages: from 85% to 99%, from 85% to 98.5%, from 85% to 98%, from 85% to 97.5%, from 85% to 97%, from 85.5% to 99.9%, from 86% to 99.9%, from 86% to 99.5%, from 86.5% to 99.5%, from 87% to 99.5%, from 87% to 99%, from 87.5% to 99.9%, from 87.5% to 99.5%, from 87.5% to 99%, from 88% to 99.9%, from 88% to 99.5%, from 88% to 99%, from 89% to 99.9%, from 89% to 99.5%, from 89% to 99%, from 89.5% to 99.9%, from 89.5% to 99.5%, from 89.5% to 99%, from 90% to 99.9%, from 90% to 99.5%, from 90% to 99.5%, from 90% to 99%, from 90% to 98.5%, from 90% to 98%, from 90% to 97.5%, from 90% to 97%, from 90% to 96.5%, from 90% to 96%, from 91% to 99.9%, from 91% to 99.5%, from 91% to 99%, from 91% to 98.5%, from 91% to 98%, from 91% to 97.5%, from 91% to 97%, from 91% to 96.5%, from 91% to 96%, from 92% to 99.9%, from 92% to 99.5%, from 92% to 99%, from 92% to 98.5%, from 92% to 98%, from 92% to 97.5%, from 92% to 97%, from 92% to 96.5%, from 92% to 96%, from 93% to 99.9%, from 93% to 99.5%, from 93% to 99%, from 93% to 98.5%, from 93% to 98%, from 93% to 97.5%, from 93% to 97%, from 93% to 96.5%, from 93% to 96%, from 94% to 99.9%, from 94% to 99.5%, from 94% to 99%, from 94% to 98.5%, from 94% to 98%, from 94% to 97.5%, from 94% to 97%, from 94% to 96.5%, from 94% to 96%, from 95% to 99.9%, from 95% to 99.5%, or from 95% to 99%; and LiTDI in one of the following molar percentages: from 15% to 1%, from 15% to 1.5%, from 15% to 2%, from 15% to 2.5%, from 15% to 3%, from 14.5% to 0.1%, from 14% to 0.1%, from 14% to 0.5%, from 13.5% to 0.5%, from 13% to 0.5%, from 13% to 1%, from 12.5% to 0.1%, from 12.5% to 0.5%, from 12.5% to 1%, from 12% to 0.1%, from 12% to 0.5%, from 12% to 1%, from 11% to 0.1%, from 11% to 0.5%, from 11% to 1%, from 10.5% to 0.1%, from 10.5% to 0.5%, from 11.5% to 1%, from 10% to 0.1%, from 10% to 0.5%, from 10% to 1%, from 10% to 1.5%, from 10% to 2%, from 10% to 2.5%, from 10% to 3%, from 10% to 3.5%, from 10% to 4%, from 9% to 0.1%, from 9% to 0.5%, from 9% to 1%, from 9% to 1.5%, from 9% to 2%, from 9% to 2.5%, from 9% to 3%, from 9% to 3.5%, from 9% to 4%, from 8% to 0.1%, from 9% to 0.5%, from 8% to 1%, from 8% to 1.5%, from 8% to 3%, from 8% to 2.5%, from 8% to 3%, from 8% to 3.5%, from 8% to 4%, from 7% to 0.1%, from 7% to 0.5%, from 7% to 1%, from 7% to 1.5%, from 7% to 2%, from 7% to 2.5%, from 7% to 3%, from 7% to 3.5%, from 7% to 4%, from 6% to 0.1%, from 6% to 0.5%, from 6% to 1%, from 6% to 1.5%, from 6% to 2%, from 6% to 2.5%, from 6% to 3%, from 6% to 3.5%, from 6% to 4%, from 5% to 0.1%, from 5% to 0.5%, or from 5% to 1%.

According to one embodiment, the mixture according to the invention comprises (preferably is composed essentially of, and preferentially consists of):

LiFSI in a molar percentage of greater than or equal to 86%, of greater than or equal to 87%, of greater than or equal to 88%, of greater than or equal to 89%, of greater than or equal to 90%, of greater than or equal to 91%, of greater than or equal to 92%, of greater than or equal to 93%, of greater than or equal to 94%, of greater than or equal to 95%, of greater than or equal to 96%, of greater than or equal to 97%, of greater than or equal to 98%, of greater than or equal to 99%;

LiTDI in a molar percentage of less than or equal to 14%, of less than or equal to 13%, of less than or equal to 12%, of less than or equal to 11%, of less than or equal to 10%, of less than or equal to 9%, of less than or equal to 8%, of less than or equal to 7%, of less than or equal to 6%, of less than or equal to 5%, of less than or equal to 4%, of less than or equal to 3%, of less than or equal to 2%, of less than or equal to 1%.

According to one embodiment, the mixture according to the invention is such that:

the molar percentage of LiFSI is greater than or equal to 95%; and the molar percentage of LiTDI is less than or equal to 5%.

According to one embodiment, the mixture according to the invention comprises (preferably is composed essentially of, and preferentially consists of):

from 86 mol % to 99.9 mol %, preferably from 90 mol % to 99.5 mol %, in particular from 92 mol % to 98 mol % and preferentially from 93 mol % to 97 mol %, for example 95 mol %, of LiFSI; and from 14 mol % to 0.1 mol %, preferably from 10 mol % to 0.5 mol %, in particular from 8 mol % to 2 mol % and preferentially from 7 mol % to 3 mol %, for example 5 mol %, of LiTDI.

The present patent application also relates to the use of a mixture as defined above in a Li-ion battery, in particular in a temperature range of between -30° C. and 65° C., preferentially between -25° C. and 60° C., preferably at a temperature of greater than or equal to 25° C., preferably of between 25° C. and 65° C., advantageously between 40° C. and 60° C. For example, the use takes place in mobile devices, for example portable telephones, cameras, tablets or portable computers, in electric vehicles or in renewable energy storage.

Electrolyte Composition

The present invention also relates to an electrolyte composition, comprising the mixture of lithium salts as defined above, at least one solvent and optionally at least one electrolytic additive.

Preferably, the composition does not comprise another alkali metal or alkaline earth metal salt than LiFSI and LiTDI.

Preferably, the composition does not comprise another lithium salt than LiFSI and LiTDI. In particular, the composition does not comprise $LiPF_6$ or LiTFSI.

In the context of the invention, "electrolyte composition", "electrolyte" and "electrolytic composition" are used interchangeably.

According to one embodiment, the molar concentration of LiFSI and LiTDI in the electrolyte composition is less than or equal to 5 mol/l, advantageously less than or equal to 4 mol/l, preferably less than or equal to 2 mol/l, preferentially less than or equal to 1.5 mol/l and in particular less than or equal to 1 mol/l.

According to one embodiment, the molar concentrations of LiFSI and LiTDI in the electrolyte composition are such that:

$$[LiFSI]+[LiTDI] \leq 1 \text{ mol/l}$$

According to one embodiment, the abovementioned electrolyte composition comprises:

from 0.85 to 0.999 mol/l of LiFSI; and from 0.15 to 0.001 mol/l of LiTDI.

According to one embodiment, the molar concentration of LiFSI in the electrolyte composition is chosen from one of the following concentrations: from 0.85 to 0.99 mol/l, from 0.85 to 0.98 mol/l, from 0.85 to 0.97 mol/l, from 0.87 to 0.99 mol/l, from 0.88 to 0.99 mol/l, from 0.89 to 0.99 mol/l, from 0.90 to 0.99 mol/l, from 0.90 to 0.98 mol/l, from 0.90 to 0.97 mol/l, from 0.90 to 0.96 mol/l, from 0.91 to 0.99 mol/l, from 0.91 to 0.98 mol/l, from 0.91 to 0.97 mol/l, from 0.91 to 0.96 mol/l, from 0.92 to 0.99 mol/l, from 0.92 to 0.98 mol/l, from 0.92 to 0.97 mol/l, from 0.92 to 0.96 mol/l, from 0.93 to 0.99 mol/l, from 0.93 to 0.98 mol/l, from 0.93 to 0.97 mol/l, from 0.93 to 0.96 mol/l, from 0.94 to 0.99 mol/l, from 0.94 to 0.98 mol/l, from 0.94 to 0.97 mol/l, from 0.94 to 0.96 mol/l, or from 0.95 to 0.99 mol/l.

According to one embodiment, the molar concentration of LiTDI in the electrolyte composition is chosen from one of the following concentrations: from 0.15 to 0.01 mol/l, from 0.15 to 0.2 mol/l, from 0.15 to 0.03 mol/l, from 0.13 to 0.01 mol/l, from 0.12 to 0.01 mol/l, from 0.11 to 0.01 mol/l, from 0.10 to 0.01 mol/l, from 0.10 to 0.02 mol/l, from 0.10 to 0.03 mol/l, from 0.10 to 0.04 mol/l, from 0.09 to 0.01 mol/l, from 0.09 to 0.02 mol/l, from 0.09 to 0.03 mol/l, from 0.09 to 0.04 mol/l, from 0.08 to 0.01 mol/l, from 0.08 to 0.02 mol/l, from 0.08 to 0.03 mol/l, from 0.08 to 0.04 mol/l, from 0.07 to 0.01 mol/l, from 0.07 to 0.02 mol/l, from 0.07 to 0.03 mol/l, from 0.07 to 0.04 mol/l, from 0.06 to 0.01 mol/l, from 0.06 to 0.02 mol/l, from 0.06 to 0.03 mol/l, from 0.06 to 0.04 mol/l, or from 0.05 to 0.01 mol/l.

According to one embodiment, the molar concentration of LiFSI in the electrolyte composition is chosen from one of the following concentrations: greater than or equal to 0.86 mol/l, greater than or equal to 0.87 mol/l, greater than or equal to 0.88 mol/l, greater than or equal to 0.89 mol/l, greater than or equal to 0.90 mol/l, greater than or equal to 0.91 mol/l, greater than or equal to 0.92 mol/l, greater than or equal to 0.93 mol/l, greater than or equal to 0.94 mol/l, greater than or equal to 0.95 mol/l, greater than or equal to 0.96 mol/l, greater than or equal to 0.97 mol/l, greater than or equal to 0.98 mol/l, or greater than or equal to 0.99 mol/l.

According to one embodiment, the molar concentration of LiTDI in the electrolyte composition is chosen from one of the following concentrations: less than or equal to 0.14 mol/l, less than or equal to 0.13 mol/l, less than or equal to 0.12 mol/l, less than or equal to 0.11 mol/l, less than or equal to 0.10 mol/l, less than or equal to 0.09 mol/l, less than or equal to 0.08 mol/l, less than or equal to 0.07 mol/l, less than or equal to 0.06 mol/l, less than or equal to 0.05 mol/l, less than or equal to 0.04 mol/l, less than or equal to 0.03 mol/l, less than or equal to 0.02 mol/l, or less than or equal to 0.01 mol/l.

According to one embodiment, the abovementioned electrolyte composition is such that:

the molar concentration of LiFSI is greater than or equal to 0.95 mol/l, and the molar concentration of LiTDI is less than or equal to 0.05 mol/l.

According to one embodiment, the abovementioned electrolyte composition comprises:

from 0.86 to 0.999 mol/l, preferably from 0.86 to 0.99 mol/l, in particular from 0.90 to 0.995 mol/l, especially from 0.92 to 0.98 mol/l and preferentially from 0.93 to 0.97 mol/l, for example 0.95 mol/l, of LiFSI; and from 0.14 to 0.001 mol/l, preferably from 0.14 to 0.01 mol/l, in particular from 0.10 to 0.005 mol/l, especially from 0.08 to 0.2 mol/l and preferentially from 0.07 to 0.03 mol/l, for example 0.05 mol/l, of LiTDI.

According to one embodiment, the electrolyte composition can comprise a solvent or a mixture of solvents, such as, for example, two, three or four different solvents.

The solvent of the electrolyte composition can be a liquid solvent, optionally gelled by a polymer, or a polar polymer solvent optionally plasticized by a liquid.

According to one embodiment, the solvent is an organic solvent, preferably an aprotic organic solvent. Preferably, the solvent is a polar organic solvent.

According to one embodiment, the solvent is chosen from the group consisting of ethers, carbonates, esters, ketones, partially hydrogenated hydrocarbons, nitriles, amides, alcohols, sulfoxides, sulfolane, nitromethane, 1,3-dimethyl-2-imidazolidinone, 1,3-dimethyl-3,4,5,6-tetrahydro-2(1H)-pyrimidinone, 3-methyl-2-oxazolidinone and of their mixtures.

Mention may be made, among the ethers, of linear or cyclic ethers, such as, for example, dimethoxyethane (DME), methyl ethers of oligoethylene glycols of 2 to 5 oxyethylene units, dioxolane, dioxane, dibutyl ether, tetrahydrofuran and their mixtures.

Mention may be made, among the esters, of phosphoric acid esters or sulfite esters. Mention may be made, for example, of methyl formate, methyl acetate, methyl propionate, ethyl acetate, butyl acetate, y-butyrolactone or their mixtures.

Mention may in particular be made, among the ketones, of cyclohexanone.

Mention may be made, among the alcohols, for example, of ethyl alcohol or isopropyl alcohol.

Mention may be made, among the nitriles, for example, of acetonitrile, pyruvonitrile, propionitrile, methoxypropionitrile, dimethylaminopropionitrile, butyronitrile, isobutyronitrile, valeronitrile, pivalonitrile, isovaleronitrile, glutaronitrile, methoxyglutaronitrile, 2-methylglutaronitrile, 3-methylglutaronitrile, adiponitrile, malononitrile and their mixtures.

Mention may be made, among the carbonates, par exemple, of cyclic carbonates, such as, for example, ethylene carbonate (EC), propylene carbonate (PC), butylene carbonate (BC), dimethyl carbonate (DMC), diethyl carbonate (DEC), ethyl methyl carbonate (EMC) (CAS No. 623-53-0), diphenyl carbonate, methyl phenyl carbonate, dipropyl carbonate (DPC), methyl propyl carbonate (MPC), ethyl propyl carbonate (EPC), vinylene carbonate (VC), fluoroethylene carbonate (FEC), trifluoropropylene carbonate or their mixtures.

The solvent which is particularly preferred is chosen from the carbonates and their mixtures. Mention may in particular be made of the following mixtures:

ethylene carbonate (EC)/propylene carbonate (PC)/dimethyl carbonate (DMC) in a 1/1/1 ratio by weight;

ethylene carbonate (EC)/propylene carbonate (PC)/diethyl carbonate (DEC) in a 1/1/1 ratio by weight;

ethylene carbonate (EC)/propylene carbonate (PC)/ethyl methyl carbonate (EMC) in a 1/1/1 ratio by weight;

ethylene carbonate (EC)/dimethyl carbonate (DMC) in a 1/1 ratio by weight;

ethylene carbonate (EC)/diethyl carbonate (DEC) in a 1/1 ratio by weight;

ethylene carbonate (EC)/ethyl methyl carbonate (EMC) in a 1/1 ratio by weight;

ethylene carbonate (EC)/dimethyl carbonate (DMC) in a ratio by weight in a 3/7 ratio by volume;

ethylene carbonate (EC)/diethyl carbonate (DEC) in a 3/7 ratio by volume;

ethylene carbonate (EC)/ethyl methyl carbonate (EMC) in a 3/7 ratio by volume.

According to one embodiment, the electrolyte composition can comprise at least one electrolytic additive.

Preferably, the electrolytic additive is chosen from the group consisting of fluoroethylene carbonate (FEC), vinylene carbonate, 4-vinyl-1,3-dioxolan-2-one, pyridazine, vinylpyridazine, quinoline, vinylquinoline, butadiene, sebaconitrile, $LiB(C_2O_4)_2$, lithium nitrate, alkyl disulfides, fluorotoluene, 1,4-dimethoxytetrafluorotoluene, oximes, aliphatic epoxides, halogenated biphenyls, methacrylic acids, allyl ethyl carbonate, vinyl acetate, divinyl adipate, acrylonitrile, 2-vinylpyridine, maleic anhydride, methyl cinnamate, phosphonates, silane compounds containing a vinyl, 2-cyanofuran and of their mixtures, the electrolytic additive preferably being fluoroethylene carbonate (FEC).

For example, the content of electrolytic additive in the electrolyte composition is between 0.01% and 10%, preferably between 0.1% and 4%, by weight, with respect to the total weight of the composition. In particular, the content of electrolytic additive in the electrolyte composition is less than or equal to 2% by weight, with respect to the total weight of the composition.

According to one embodiment, the electrolyte composition according to the invention is chosen from one of the following compositions:

i) 0.85 mol/l of LiFSI and 0.15 mol/l of LiTDI, fluoroethylene carbonate as electrolytic additive (in particular at a content of less than or equal to 2% by weight), mixture of EC/EMC in a 3/7 ratio by volume as solvent;

ii) 0.90 mol/l of LiFSI and 0.10 mol/l of LiTDI, fluoroethylene carbonate as electrolytic additive (in particular at a content of less than or equal to 2% by weight), mixture of EC/EMC in a 3/7 ratio by volume as solvent;

iii) 0.95 mol/l of LiFSI and 0.05 mol/l of LiTDI, fluoroethylene carbonate as electrolytic additive (in particular at a content of less than or equal to 2% by weight), mixture of EC/EMC in a 3/7 ratio by volume as solvent;

iii) 0.96 mol/l of LiFSI and 0.04 mol/l of LiTDI, fluoroethylene carbonate as electrolytic additive (in particular at a content of less than or equal to 2% by weight), mixture of EC/EMC in a 3/7 ratio by volume as solvent;

iv) 0.97 mol/l of LiFSI and 0.03 mol/l of LiTDI, fluoroethylene carbonate as electrolytic additive (in particular at a content of less than or equal to 2% by weight), mixture of EC/EMC in a 3/7 ratio by volume as solvent;

v) 0.98 mol/l of LiFSI and 0.02 mol/l of LiTDI, fluoroethylene carbonate as electrolytic additive (in particular at a content of less than or equal to 2% by weight), mixture of EC/EMC in a 3/7 ratio by volume as solvent;

vi) 0.99 mol/l of LiFSI and 0.01 mol/l of LiTDI, fluoroethylene carbonate as electrolytic additive (in particular at a content of less than or equal to 2% by weight), mixture of EC/EMC in a 3/7 ratio by volume as solvent.

The composition, preferably the electrolyte composition, can be prepared by dissolution, preferably with stirring, of the salts in appropriate proportions of solvent(s).

The present patent application also relates to the use of an electrolyte composition as defined above in a Li-ion battery, in particular in a temperature range of between −30° C. and 65° C., preferentially between −25° C. and 60° C., preferably at a temperature of greater than or equal to 25° C., preferably of between 25° C. and 65° C., advantageously between 40° C. and 60° C. For example, the use takes place in mobile devices, for example portable telephones, cameras, tablets or portable computers, in electric vehicles or in renewable energy storage.

Electrochemical Cell

The present patent application also relates to an electrochemical cell comprising a negative electrode, a positive electrode and an electrolyte composition as defined here above, interposed between the negative electrode and the positive electrode. The electrochemical cell can also comprise a separator, in which the electrolyte composition as defined above is impregnated.

The present invention also relates to a battery comprising at least one electrochemical cell as described above. When the battery comprises several electrochemical cells according to the invention, said cells can be assembled in series and/or in parallel.

In the context of the invention, negative electrode is understood to mean the electrode which acts as anode when the battery produces current (that is to say, when it is in the process of discharging) and which acts as cathode when the battery is in the process of charging.

The negative electrode typically comprises an electrochemically active material, optionally an electron-conducting material, and optionally a binder.

In the context of the invention, "electrochemically active material" is understood to mean a material capable of reversibly inserting ions.

In the context of the invention, "electron-conducting material" is understood to mean a material capable of conducting electrons.

According to one embodiment, the negative electrode of the electrochemical cell comprises, as electrochemically active material, graphite, lithium, a lithium alloy, a lithium titanate of $Li_4Ti_5O_{12}$ or $TiO_2$ type, silicon or a lithium/silicon alloy, a tin oxide, a lithium intermetallic compound or one of their mixtures.

The negative electrode can comprise lithium; the latter can then consist of a film of metal lithium or of an alloy comprising lithium. An example of negative electrode can comprise an active lithium film prepared by rolling a strip of lithium between rollers.

In the context of the invention, positive electrode is understood to mean the electrode which acts as cathode when the battery produces current (that is to say, when it is in the process of discharging) and which acts as anode when the battery is in the process of charging.

The positive electrode typically comprises an electrochemically active material, optionally an electron-conducting material, and optionally a binder.

In another embodiment, the positive electrode of the electrochemical cell comprises an electrochemically active material chosen from manganese dioxide ($MnO_2$), iron oxide, copper oxide, nickel oxide, lithium/manganese composite oxides (for example $Li_xMn_2O_4$ or $Li_xMnO_2$), lithium/nickel composition oxides (for example $Li_xNiO_2$), lithium/cobalt composition oxides (for example $Li_xCoO_2$), lithium/nickel/cobalt composite oxides (for example $LiNi_{1-y}Co_yO_2$), lithium/nickel/cobalt/manganese composite oxides (for example $LiNi_xMn_yCo_zO_2$ with x+y+z=1), lithium-enriched lithium/nickel/cobalt/manganese composite oxides (for example $Li_{1+x}(NiMnCo)_{1-x}O_2$), lithium/transition metal composite oxides, lithium/manganese/nickel composite oxides of spinel structure (for example $Li_xMn_{2-y}Ni_yO_4$), lithium/phosphorus oxides of olivine structure (for example $Li_xFePO_4$, $Li_xFe_{1-y}Mn_yPO_4$ or $Li_xCoPO_4$), iron sulfate, vanadium oxides and their mixtures.

Preferably, the positive electrode is comprises an electrochemically active material chosen from $LiCoO_2$, $LiFePO_4$ (LFP), $LiMn_xCo_yNi_zO_2$ (NMC, with x+y+z=1), $LiFePO_4F$, $LiFeSO_4F$, $LiNiCoAlO_2$ and their mixtures.

The material of the positive electrode can also comprise, besides the electrochemically active material, an electron-conducting material, such as a carbon source, including, for example, carbon black, Ketjen® carbon, Shawinigan carbon, graphite, graphene, carbon nanotubes, carbon fibers (such as vapor-grown carbon fibers (VGCF)), non-powdery carbon obtained by carbonization of an organic precursor, or a combination of two or more of these. Other additives can also be present in the material of the positive electrode, such as lithium salts or inorganic particles of ceramic or glass type, or also other compatible active materials (for example sulfur).

The material of the positive electrode can also comprise a binder. Nonlimiting examples of binders comprise linear, branched and/or crosslinked polyether polymer binders (for example polymers based on poly(ethylene oxide) (PEO), or poly(propylene oxide) (PPO) or on a mixture of the two (or an EO/PO copolymer), and optionally comprising crosslinkable units), water-soluble binders (such as SBR (styrene/butadiene rubber), NBR (acrylonitrile/butadiene rubber), HNBR (hydrogenated NBR), CHR (epichlorohydrin rubber), ACM (acrylate rubber)), or binders of fluoropolymer type (such as PVDF (polyvinylidene fluoride), PTFE (polytetrafluoroethylene)), and their combinations. Some binders, such as those which are soluble in water, can also comprise an additive, such as CMC (carboxymethylcellulose).

The mixture of salts according to the invention advantageously has a good ionic conductivity in solution. Furthermore, the mixture of salts according to the invention advantageously makes it possible to improve the power performance qualities of the battery, which makes it possible, for example, to more quickly recharge the battery, or also to provide the power necessary in the event of an energy peak.

The mixture of salts according to the invention also advantageously makes it possible to have good performance qualities, in particular in terms of power, over a wide temperature range, for example under cold conditions, or over a temperature range extending from approximately -25° C. to approximately 60° C.

In the context of the invention, the term "of between x and y" or "between x and y" is understood to mean an interval in which the limits x and y are included. For example, the range "of between 85% and 99.9%" or "ranging from 85% to 99.9%" includes in particular the values 85% and 99.9%.

All the embodiments described above can be combined with one another.

The following examples illustrate the invention without, however, limiting it.

Experimental Part

Abbreviations

EC: ethylene carbonate
EMC: ethyl methyl carbonate
FEC: fluoroethylene carbonate Suppliers EC: BASF Corporation
EMC: BASF Corporation
FEC: BASF Corporation The LiFSI used is obtained in particular by the process described in the application WO2015/158979, while the LiTDI results from the process described in the application WO2013/072591.

EXAMPLE 1

Ionic Conductivity Measured by Impedance Spectroscopy

Two electrolytes were prepared according to the following compositions:
  composition 1 (according to the invention): 0.95M LiFSI, 0.05M LiTDI, mixture of solvents EC/EMC (ethylene carbonate/ethyl methyl carbonate) 3/7 (ratio by volume), 2% by weight of FEC (with respect to the total weight of the composition);
  composition 2 (comparative): 0.80M LiFSI, 0.20M LiTDI, mixture of solvents EC/EMC 3/7 (ethylene carbonate/ethyl methyl carbonate) (ratio by volume), 2% by weight of FEC (with respect to the total weight of the composition).

A conductivity cell is then immersed in each of the solutions and three impedance spectroscopy determinations were carried out. These spectroscopy determinations are carried out between 500 mHz and 100 kHz with an amplitude of 10 mV. The constant of the cell used is 1.12 and the ionic conductivity is calculated according to the following formula:

$$\sigma = \frac{1}{R} \times 1.12$$

with R representing the resistance which is obtained by linear regression of the curve $Im(Z)=f(Re(Z))$. In the specific case of $Im(Z)=0$, R is equal to the opposite of the ordinate at the origin divided by the director coefficient of the equation of the linear regression.

| Composition | Conductivity (mS/cm) | R1 | R2 | R3 | Mean R |
|---|---|---|---|---|---|
| 1 | 14.66 | 75.72 | 76.4 | 77.13 | 76.417 |
| 2 | 13.50 | 82.56 | 83.4 | 83 | 82.987 |

The 0.95M LiFSI/0.05M LiTDI mixture advantageously exhibits a better ionic conductivity than the 0.8 LiFSI/0.2 LiTDI mixture.

EXAMPLE 2

Power Test

A Ragone plot test was carried out with the following compositions 1 and 2:
  composition 1 (according to the invention): 0.95M LiFSI, 0.05M LiTDI, mixture of solvents EC/EMC (ethylene carbonate/ethyl methyl carbonate) 3/7 (ratio by volume), 2% by weight of FEC (with respect to the total weight of the composition);
  composition 2 (comparative): 0.80M LiFSI, 0.20M LiTDI, mixture of solvents EC/EMC (ethylene carbonate/ethyl methyl carbonate) 3/7 (ratio by volume), 2% by weight of FEC (with respect to the total weight of the composition).

Method: the method consists in increasing the rate of discharge of a battery in order to observe the ability of the electrolyte to be able to respond to the stress imposed by the electrical circuit.

System Used:
  Cathode: $LiNi_{0.33}Mn_{0.33}Co_{0.33}O_2$ (89%), carbon fiber VGCF (2.5%), carbon black (2.5%) and 6% of PVDF binder.
Anode: Lithium Metal The current was varied between 2.7 and 4.2 V, with the discharges carried out in the following order: C/20, C/10, C/5, C/2, C and 2C.

Two C/20 formation cycles are carried out before the study in order to form all the passivation layers.

Results:
The results observed are as follows:

| Composition 1 (invention) | | |
|---|---|---|
| | Discharge | Ragone |
| 1 | C/20 | 100 |
| 2 | C/10 | 103.673781 |
| 3 | C/5 | 104.59516 |
| 4 | C/2 | 103.072243 |
| 5 | C | 99.3299947 |
| 6 | 2 C | 92.1065553 |

| Composition 2 (comparative) | | |
|---|---|---|
| | Discharge | Ragone |
| 1 | C/20 | 100 |
| 2 | C/10 | 102.160088 |
| 3 | C/5 | 100.057551 |
| 4 | C/2 | 94.490528 |
| 5 | C | 89.4708167 |
| 6 | 2 C | 84.5363772 |

The results show that composition 1 makes it possible to operate at higher power ratings than composition 2. These high ratings are particularly desired in commercial batteries in the context of mobile devices which require ever more power, and electric vehicles which, due to their low operating radius, require rapid recharges and thus electrolytes which make it possible to operate at high ratings.

The invention claimed is:
1. An electrolyte composition comprising a lithium salt mixture, wherein the lithium salt mixture comprises:
  from 85 mol % to 99.9 mol % of lithium bis(fluorosulfonyl)imide; and
  from 0.1 mol % to 15 mol % of lithium 2-trifluoromethyl-4,5-dicyanoimidazolate,
  wherein the electrolyte composition further comprises at least one solvent and at least one electrolytic additive in addition to the lithium salt mixture,
  wherein the at least one solvent is chosen from the group consisting of dimethoxyethane, dioxolane, dioxane, dibutyl ether, tetrahydrofuran, carbonates, esters, ketones, partially hydrogenated hydrocarbons, nitriles, amides, alcohols, sulfoxides, sulfolane, nitromethane,

1,3-dimethyl-2-imidazolidinone, 1,3-dimethyl-3,4,5,6-tetrahydro-2(1H)- pyrimidinone, 3-methyl-2-oxazolidinone and their mixtures, wherein the content of the electrolytic additive in the electrolyte composition is between 0.01 wt % and 10 wt %.

2. The composition as claimed in claim 1, comprising:
lithium bis(fluorosulfonyl)imide in one of the following molar percentages: from 85% to 99%, from 85% to 98.5%, from 85% to 98%, from 85% to 97.5%, from 85% to 97%, from 85.5% to 99.9%, from 86% to 99.9%, from 86% to 99.5%, from 86.5% to 99.5%, from 87% to 99.5%, from 87% to 99%, from 87.5% to 99.9%, from 87.5% to 99.5%, from 87.5% to 99%, from 88% to 99.9%, from 88% to 99.5%, from 88% to 99%, from 89% to 99.9%, from 89% to 99.5%, from 89% to 99%, from 89.5% to 99.9%, from 89.5% to 99.5%, from 89.5% to 99%, from 90% to 99.9%, from 90% to 99.5%, from 90% to 99.5%, from 90% to 99%, from 90% to 98.5%, from 90% to 98%, from 90% to 97.5%, from 90% to 97%, from 90% to 96.5%, from 90% to 96%, from 91% to 99.9%, from 91% to 99.5%, from 91% to 99%, from 91% to 98.5%, from 91% to 98%, from 91% to 97.5%, from 91% to 97%, from 91% to 96.5%, from 91% to 96%, from 92% to 99.9%, from 92% to 99.5%, from 92% to 99%, from 92% to 98.5%, from 92% to 98%, from 92% to 97.5%, from 92% to 97%, from 92% to 96.5%, from 92% to 96%, from 93% to 99.9%, from 93% to 99.5%, from 93% to 99%, from 93% to 98.5%, from 93% to 98%, from 93% to 97.5%, from 93% to 97%, from 93% to 96.5%, from 93% to 96%, from 94% to 99.9%, from 94% to 99.5%, from 94% to 99%, from 94% to 98.5%, from 94% to 98%, from 94% to 97.5%, from 94% to 97%, from 94% to 96.5%, from 94% to 96%, from 95% to 99.9%, from 95% to 99.5%, or from 95% to 99%; and
lithium 2-trifluoromethyl-4,5-dicyanoimidazolate in one of the following molar percentages: from 15% to 1%, from 15% to 1.5%, from 15% to 2%, from 15% to 2.5%, from 15% to 3%, from 14.5% to 0.1%, from 14% to 0.1%, from 14% to 0.5%, from 13.5% to 0.5%, from 13% to 0.5%, from 13% to 1%, from 12.5% to 0.1%, from 12.5% to 0.5%, from 12.5% to 1%, from 12% to 0.1%, from 12% to 0.5%, from 12% to 1%, from 11% to 0.1%, from 11% to 0.5%, from 11% to 1%, from 10.5% to 0.1%, from 10.5% to 0.5%, from 11.5% to 1%, from 10% to 0.1%, from 10% to 0.5%, from 10% to 1%, from 10% to 1.5%, from 10% to 2%, from 10% to 2.5%, from 10% to 3%, from 10% to 3.5%, from 10% to 4%, from 9% to 0.1%, from 9% to 0.5%, from 9% to 1%, from 9% to 1.5%, from 9% to 2%, from 9% to 2.5%, from 9% to 3%, from 9% to 3.5%, from 9% to 4%, from 8% to 0.1%, from 9% to 0.5%, from 8% to 1%, from 8% to 1.5%, from 8% to 3%, from 8% to 2.5%, from 8% to 3%, from 8% to 3.5%, from 8% to 4%, from 7% to 0.1%, from 7% to 0.5%, from 7% to 1%, from 7% to 1.5%, from 7% to 2%, from 7% to 2.5%, from 7% to 3%, from 7% to 3.5%, from 7% to 4%, from 6% to 0.1%, from 6% to 0.5%, from 6% to 1%, from 6% to 1.5%, from 6% to 2%, from 6% to 2.5%, from 6% to 3%, from 6% to 3.5%, from 6% to 4%, from 5% to 0.1%, from 5% to 0.5%, or from 5% to 1%.

3. The composition as claimed in claim 1, in which:
the molar percentage of lithium bis(fluorosulfonyl)imide is greater than or equal to 95%; and
the molar percentage of lithium 2-trifluoromethyl-4,5-dicyanoimidazolate is between 0.1% and 5%.

4. The composition as claimed in claim 1, comprising:
from 86 mol % to 99.9 mol % of lithium bis(fluorosulfonyl)imide; and
from 14 mol % to 0.1 mol % of lithium 2-trifluoromethyl-4,5-dicyanoimidazolate.

5. The composition as claimed in claim 1, in which the molar concentration of lithium bis(fluorosulfonyl)imide and lithium 2-trifluoromethyl-4,5-dicyanoimidazolate in the electrolyte composition is between 0.85 mol/l and 5 mol/l.

6. The composition as claimed in claim 1, comprising:
from 0.85 to 0.999 mol/l of lithium bis(fluorosulfonyl)imide; and
from 0.15 to 0.001 mol/l of lithium 2-trifluoromethyl-4,5-dicyanoimidazolate.

7. The composition as claimed in claim 1, comprising:
from 0.86 to 0.999 mol/l of lithium bis(fluorosulfonyl)imide; and
from 0.14 to 0.001 mol/l of lithium 2-trifluoromethyl-4,5-dicyanoimidazolate.

8. The composition as claimed in claim 1, in which the solvent is chosen from carbonates and their mixtures.

9. The composition as claimed in claim 1, in which the electrolytic additive is chosen from the group consisting of fluoroethylene carbonate, vinylene carbonate, 4-vinyl-1,3-dioxolan-2-one, pyridazine, vinylpyridazine, quinoline, vinylquinoline, butadiene, sebaconitrile, $LiB(C_2O_4)_2$, lithium nitrate, alkyl disulfides, fluorotoluene, 1,4-dimethoxytetrafluorotoluene, oximes, aliphatic epoxides, halogenated biphenyls, methacrylic acids, allyl ethyl carbonate, vinyl acetate, divinyl adipate, acrylonitrile, 2-vinylpyridine, maleic anhydride, methyl cinnamate, phosphonates, silane compounds containing a vinyl, 2-cyanofuran, and mixtures thereof.

10. A method of operating a Li-ion battery, the battery comprising an electrolyte composition as claimed in claim 1, wherein the method comprises operating the battery at a temperature range of between −30° C. and 65° C.

11. An electrochemical cell comprising a negative electrode, a positive electrode and an electrolyte composition as claimed in claim 1, interposed between the negative electrode and the positive electrode.

12. A battery comprising at least one electrochemical cell as claimed in claim 11.

13. The composition as claimed in claim 1, wherein the mixture comprises:
from 95 mol % to 99.9 mol % of lithium bis(fluorosulfonyl)imide; and
from 0.1 mol % to 5 mol % of lithium 2-trifluoromethyl-4,5-dicyanoimidazolate.

14. A method of operating a Li-ion battery, the battery comprising the composition as claimed in claim 13, wherein the method comprises operating the battery at a temperature range of between −30° C. and 65° C.

* * * * *